United States Patent [19]

Havira

[11] 4,382,290
[45] May 3, 1983

[54] APPARATUS FOR ACOUSTICALLY INVESTIGATING A BOREHOLE

[75] Inventor: R. Mark Havira, New Fairfield, Conn.

[73] Assignee: Schlumberger Technology Corporation, Tex.

[21] Appl. No.: 164,073

[22] Filed: Jun. 30, 1980

Related U.S. Application Data

[60] Division of Ser. No. 911,016, May 30, 1978, Pat. No. 4,255,798, which is a continuation-in-part of Ser. No. 814,588, Jul. 11, 1977, abandoned.

[51] Int. Cl.³ .................. G01V 1/40; G01V 1/00
[52] U.S. Cl. ......................... 367/35; 181/104; 181/105; 367/86
[58] Field of Search .......... 181/104, 105; 367/25, 367/86, 151, 152

[56] References Cited

U.S. PATENT DOCUMENTS

| | | | |
|---|---|---|---|
| 3,504,758 | 4/1970 | Dueker | 181/104 |
| 3,504,759 | 4/1970 | Cubberly, Jr. | 181/104 |
| 3,974,476 | 8/1976 | Cowles | 181/104 X |
| 4,084,582 | 4/1978 | Nigam | 367/151 X |

FOREIGN PATENT DOCUMENTS

399814  2/1974  U.S.S.R. ................. 181/104

Primary Examiner—Maynard R. Wilbur
Assistant Examiner—Kenneth R. Kaiser
Attorney, Agent, or Firm—Kenneth Olsen; Louis H. Reens

[57] ABSTRACT

An apparatus is described for acoustically investigating a casing in a borehole with a source of acoustic energy that is directed at the reflecting surface of an acoustic reflector in front of which is an acoustically transparent window. The inclination of the window relative to the reflecting surface is selected to deflect secondary transmissions and thus reduce window produced interferences. Several embodiments are described.

4 Claims, 8 Drawing Figures

APPARATUS FOR ACOUSTICALLY INVESTIGATING A BOREHOLE

This is a division of application Ser. No. 911,016 filed May 30, 1978, now U.S. Pat. No. 4,255,798, which is a continuation-in-part of application Ser. No. 814,588 filed July 11, 1977, now abandoned.

FIELD OF THE INVENTION

This invention relates to methods and apparatuses for acoustically investigating a borehole. More specifically, this invention relates to a method and apparatus using an acoustic pulse echo technique for investigating the quality of the cement bond to a casing and the thickness of the casing located in a borehole.

BACKGROUND OF THE INVENTION

In a well completion, a string of casing or pipe is set in a well bore and cement is forced into the annulus between the casing and the well bore, primarily to separate oil and gas producing horizons from each other and from water-bearing strata.

If the cement fails to provide a separation of one zone from another, then fluids under pressure from one zone may be able to migrate and contaminate an otherwise productive nearby zone. Migration of water in particular produces undesirable water cutting of a producing zone and possibly can make a well noncommercial.

Cement failures can occur in a variety of manners. For example, there may, for one reason or another, be a complete absence of cement behind the casing segment where the cement should be. This would be a gross cement bonding failure leading to rapid contamination between zones intended to be separated.

Another type of cement failure arises when the cement is present behind the casing, but a small cement-free annulus exists between the cement and casing. This annulus may be so thick as to enable hydraulic communication between zones leading to undesirable contamination.

Such annulus, however, may also be so thin as to effectively preserve the hydraulic security function of the cement. Such acceptable small annulus may arise from the technique employed to introduce the cement in the first place. For example, the cement typically is introduced under very high pressure such as produced by using a heavy mud to chase the cement plug down and into the annulus around the casing. The resulting pressure inside the casing causes a slight expansion of the casing and subsequent contraction when the heavy mud is removed. The magnitude of the contraction depends upon the pressure and casing thickness and tends to result in a slight separation, an annulus, between the cement and casing. It is important to know whether the cement is performing its function, i.e. whether the cement bond is hydraulically secure.

Techniques have been proposed to ascertain the quality of the cement bond. In this sense the term "bond" as used herein, is to be understood to include both those cases where the cement actually adheres to the casing as well as when there is no adhesion but instead a small micro-annulus which is so small as to prevent fluid communication between cement separated zones. In other words, the term "good bond" means that separation of zones by the cement is adequate to prevent fluid migration between the zones even in the presence of a micro-annulus. It is, therefore, desirable that cement evaluation techniques identify such micro-annuli as good cement bonds while recognizing annuli incapable of separating zones as hydraulically insecure or bad bonds.

When an acoustic pulse producer such as described in Norel et al is employed in an ultrasonic echo testing device as described in Russian Patent SU No. 405095 or the U.S. Pat. No. 3,974,476 to Cowles, the increased spacing suggested by the latter between the transducer and the casing enables reception of a greater number of cycles. However, in such case the intermediate layers proposed by Norel et al between the transducer and the casing tend to severely attenuate the echo signals which already arrive with reduced amplitude by virtue of the increased spacing.

SUMMARY OF THE INVENTION

As described with reference to several embodiments for investigating the casing, a tool is used having either an acoustic source, which is rotated as the tool is moved along a cased borehole, or which has a plurality of circumferentially distributed acoustic sources. With such tool discrete radial casing segments can be inspected with good circumferential resolution. If desired, a precise location of flaws in the casing thickness or cement bond can be obtained by providing azimuth tool orientation information.

The term radial segment as used herein means the segment of the casing extending between its walls and surrounding a given radius which extends generally normal to the casing wall from the center of the casing.

In an apparatus for acoustic borehole investigation in accordance with the invention, acoustic pulses are directed at a reflecting surface of a rotating reflector which reflects the pulses through an acoustically transparent window. The window has a predetermined inclination relative to that of the reflecting surface so as to reduce secondary acoustic transmissions and window caused interferences. In one form the window is of an annular construction and a rotating reflector extends from above to below the window to form a structural reinforcement that extends to below the annular window.

It is, therefore, an object of the invention to provide an improved apparatus for acoustically investigating a borehole.

These and other advantages and objects of the invention can be understood from the following description of several embodiments described in detail in conjunction with the drawings.

DETAILED DESCRIPTION OF EMBODIMENTS

FIGS. 1, 2, 3, 4 and 5

Figures 1, 2, 3:
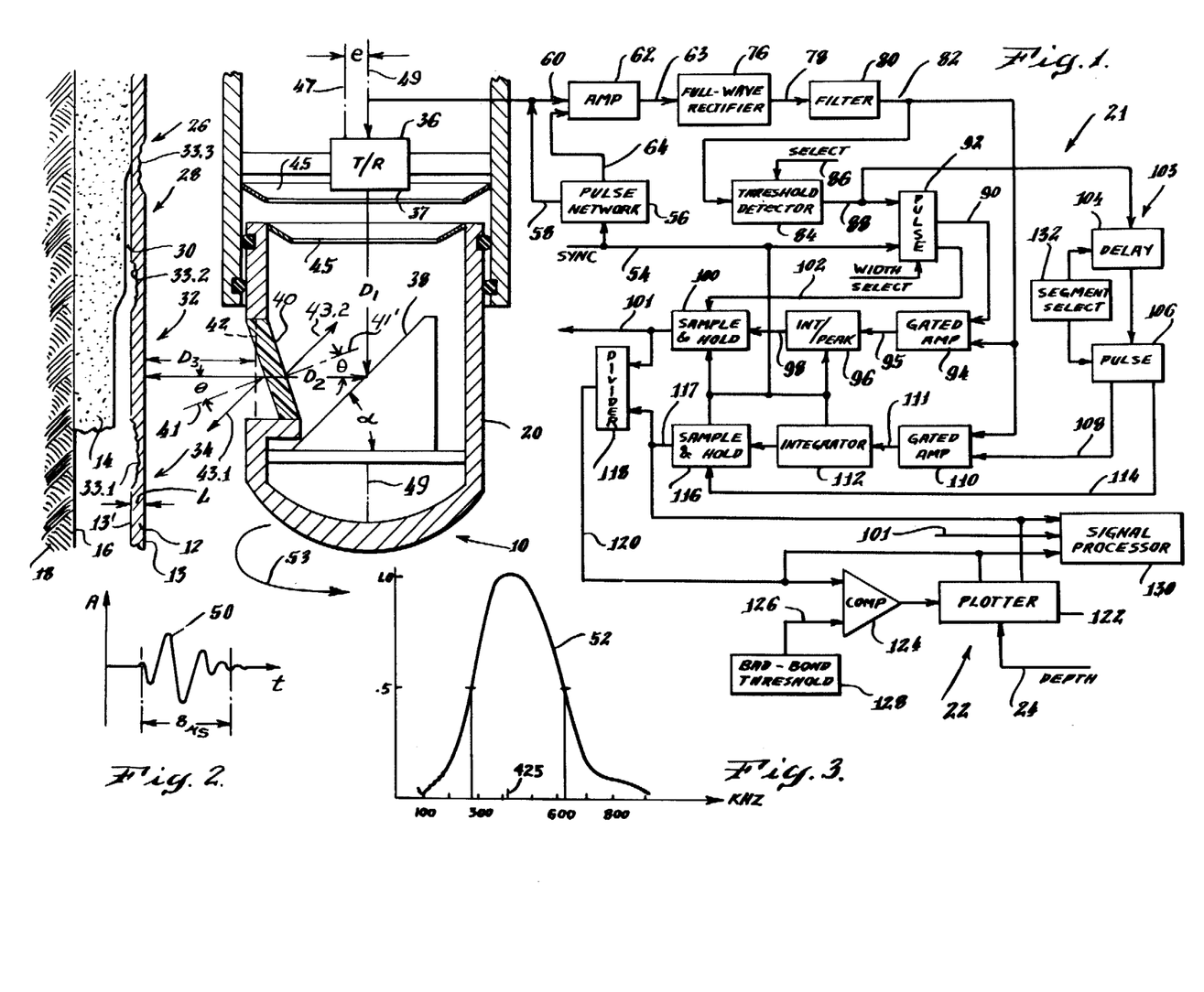
FIG. 1 is a schematic representation of one apparatus for evaluating the quality of the cement bond and/or the thickness of the casing in accordance with the invention.
FIG. 2 is a waveform representation of a preferred acoustic pulse generated in the apparatus shown in FIG. 1.
FIG. 3 is a plot of the frequency spectrum of the acoustic pulse shown in FIG. 2.

With reference to FIGS. 1 through 3, a system 10 is illustrated for acoustically investigating the quality of the cement bond between a casing 12 and an annulus of cement 14 in a borehole 16 formed in an earth formation 18. An acoustic pulse producing tool 20 is suspended inside the casing 12 with a cable (not shown) having signal paths along which signals for control of tool 20 and for its observations are transmitted between a signal processor 21 in tool 20 and surface located controls and signal processing equipment such as shown at 22. A depth signal, representative of the depth in borehole 14 of tool 20, is derived on a line 24 with a conventional depth monitor (not shown) coupled to the cable with which the tool 20 is moved along casing 12.

The cylindrical casing 12 is shown in partial section as well as the surrounding cement annulus 14. The shape of the borehole 16 is shown as uniform and the casing correspondingly illustrated as equidistantly spaced from the borehole wall. In practice, however, the borehole wall is likely to be irregular with crevasses and cracks. Hence, the cement annulus 14 may vary in thickness and the spacing between the casing 12 and the formation 18 may vary.

The cement 14 is shown with various bond states frequently encountered. At region 26 the cement is shown as adhering to the casing 12 while at 28 a microannulus, $\mu a$, 30, which is hydraulically secure, occurs. In the region 32 the annulus 30 is shown enlarged to a thickness with which vertical zone separation is no longer obtainable while at region 34 the cement is entirely absent. The cement-free regions at 28, 32 and 34 normally are filled with water or a combination of water and mud. These cement conditions do not necessarily occur as illustrated and are shown here for purposes of illustrating the invention. Suffice it to note that the cement conditions at regions 26 and 30 are to be evaluated as good bonds while those at regions 32 and 34 must be detected as bad.

Casing 12 is further shown with externally corroded segments 33.1, 33.2 and an internally corroded segment 33.3 where the casing wall has been reduced in thickness. Such corrosions may occur at other regions and can be particularly harmful when one occurs in a region leading to hydraulic communication between zones which must remain isolated from each other. The illustrated corroded segments 33.1-33.3 may appear as actual gaps or occur as scaly segments which present a rough surface appearance and may even partially separate from the good parent metal. The scaly segments become saturated by the borehole fluid segments so that acoustic investigation of the good parent metal beneath the scaly segments can still be made.

The tool 20 fits within the casing 12 which normally is filled with water or a mixture of water and mud. The tool 20 is kept central in the casing 12 with appropriate centralizers (not shown) as are well known in the art. In the practice of the invention the tool 20 preferably is kept parallel to the casing wall, though the tool may be displaced relative to the central axis of the casing 12. As will be further explained with reference to FIG. 1, some compensation for tilt conditions, i.e. when the tool 20 forms an angle with the casing axis, is obtained with the system 10.

Tool 20 is further provided with a transducer 36 functioning as a pulse transmitter and receiver. In some instances the transmitter and receiver functions can be produced by separate devices. The transducer 36 is oriented to direct an acoustic pulse onto an acoustic reflector 38 and then through a window 40 onto a selected radial segment of the casing 12. The acoustic pulse is partially passed through casing 12 and partially trapped in casing 12 with reverberations occurring in the radial segment at the thickness resonance of the casing.

The nature of the window 40 may vary and preferably is formed of such material and so inclined relative to the direction of travel of the acoustic pulses from transmitter 36 that the acoustic returns can pass through with a minimum of attenuation and source of reflections. Window 40 can be made of polyurethane such as sold by the Emerson-Cummings Company as CPC-41 having an acoustic velocity of about 1,700 meters/second and a density of about 1.1 grams/cm$^3$. Such material exhibits a similar acoustic impedance as a fluid placed in the space between source 36, reflector 38 and window 40 to equalize pressure across window 40.

The fluid with which the space inside the tool between the transducer 36, and window 40 is filled is preferably selected for low or minimum attentuation and an acoustic impedance which will not contrast too widely from that of the borehole fluid in the frequency range of interest. An acceptable fluid may, for example, be ethylene glycol.

Window 40 is inclined at an angle $\theta$ which is defined as the angle between the direction of propagation of the initial acoustic pulse from transducer 36 and the normal 41 to the window surface area upon which this acoustic pulse is incident. Such inclination serves to deflect secondary transmissions such as 43.1 in a direction which avoids window produced interference. Suitable annular acoustic absorbing surfaces such as baffles 45 may be used inside the tool to trap and absorb acoustic reflections 43.2 from the inside wall of window 40. The size of the angle $\theta$ may be of the order of 20° to 30" as suggested in the U.S. Pat. No. 3,504,758 to Dueker.

Although the inclination of window 40 could be in a direction measured relative to the incident beam travel path, as shown in the U.S. Pat. No. 3,504,758 to Dueker, or U.S. Pat. No. 3,504,759 to Cubberly, the preferred orientation is as illustrated in FIG. 1 herein to enable use of a larger reflector 38.

The size of reflector 38 is significant in that the reflector surface area influences focusing of the acoustic energy onto the casing 12 and the capture of a sufficient acoustic return for improved signal to noise ratio.

If the reflectors of Dueker or Cubberly are enlarged, the internal reflections from their windows are likely to be intercepted by the reflectors and redirected onto the receiver transducer in interference with the desired acoustic returns from the casing. When a window inclination as illustrated in FIG. 1 herein is employed, however, a large reflector 38 can be used, with effective dimensions sufficient to either focus or preserve the beam shape of the acoustic energy directed onto casing 12 and provide a significant acoustic return to receiver transducer 36.

The inclination of window 40 can be clearly distinguished from that employed in Dueker or Cubberly with reference to the orientation of the internal window normal 41' relative to the point of incidence of the acoustic beam along its travel path $D_2$ from reflector 38. When as shown in FIG. 1, the normal 41' lies between the beam travel path $D_2$ and the acoustic receiver function of transducer 36, the inclination angle and also the angle of incidence, can be considered as positive. This angle would also be positive when the internal normal lies between the beam travel path and a separate acoustic receiver such as employed in the acoustic borehole apparatus illustrated in the previously identified Russian Patent SU No. 405,095.

In case of a window oriention as shown in the Dueker or Cubberly patents, the inclination angle or angle of incidence can be construed as negative because the internal window normal is on the other side of the acoustic beam travel path and points away from the receiver transducer.

With the window inclination as illustrated in FIG. 1, care should be taken to avoid directing reflections such as 43.2 onto the transducer 36; the inclination angle, therefore, should be positive and sufficiently large. However, the inclination angle should be not so large that reflections such as 43.2 fail to be either absorbed or intercepted by baffles 45.

A portion of the acoustic pulse is passed through casing 12 and, in turn, is partially reflected by the next interface, which in region 26 would be cement material, while at the regions 28, 32 would be the annulus 30 and water-mud at region 34.

In the embodiment of FIG. 1 the acoustic transducer 36 is selectively located so that its effective spacing (the travel time for an acoustic pulse) to the casing 12 is sufficiently long to permit isolation of interference from secondary transmission caused when the strong acoustic casing reflection is again partially reflected by either a window or the transducer 36 back to casing 12 to produce new reverberations and secondary acoustic returns. A desired total spacing D is obtained by locating the transducer 36 generally at an axial distance $D_1$ from reflector 38, which in turn is spaced a distance $D_2$ from the casing 12.

The total distance $D = D_1 + D_2$ between transducer 36 and casing 12 is further selected sufficiently long so that the desired acoustic returns including those attributable to reverberations trapped between the casing inner and outer walls 13 and 13' respectively can be detected. The total distance D is thus sufficiently long to include those acoustic returns prior to their decay to some small value as a result of leakage into adjoining media. On the other hand, the total spacing D is kept sufficiently small to avoid undue attenuation by the mud external to tool 20 and the fluid inside tool 20.

In addition to these spacing considerations, the distance $D_1$ between transducer 36 and reflector 38 has been found to affect the sensitivity of the system to tool positions away from a concentric relationship with the central axis 47 of casing 12. It should be understood that tool 20 is provided with suitable centralizers, not shown, as are generally well known. Despite the presence of such centralizers some tool displacement, shown as an eccentricity distance e between the casing axis 47 and tool axis 49, may arise from a number of conditions inside casing 12. The distance $D_1$, for this reason is selected to tolerate a maximum amount of tool eccentricity e.

The optimum value for the spacing $D_1$ depends further upon such factors as the effective dimensions of surface 37 of transducer 36 such as its diameter in case of a disk transducer 36.

For a disk transducer having a diameter of the order of about one inch to produce a pulse such as 50 in FIG. 2 with a frequency spectrum such as 52 in FIG. 3, the total distance $D_1$ is generally of the order between about 2 to about 3 inches.

A basis for selecting the total distance D is thus to assure sufficient time to receive all those acoustic returns which significantly contribute to an accurate judgment as to the quality of the cement bond in the presence of a small casing-cement annulus. The total distance D should be long enough to enable the portion in the acoustic returns attributable to a bad cement bond to be received free from interference.

The acoustic returns include acoustic reflections arising as a result of the interaction of the initial acoustic pulse with various media. A first acoustic casing reflection arises from the interface between the water or mud inside the casing 12 and the inside casing wall 13. This first reflection tends to be consistently the same, varying with mud consistency, inside casing wall condition, and tilts of tool 20. Subsequent acoustic returns arise as a function of reflections from successive media as well as the leakage of acoustic reverberations entrapped inside the casing.

Thus, after the first casing reflection, the acoustic portion transferred into casing 12 is now reverberating inside the casing walls 13-13' and leaking energy at each reflection. The energy lost depends upon the coefficients of reflections $r_0$ (the reflection coefficient between the fluid inside casing 12 and the casing) and $r_1$ (the reflection coefficient between casing 12 and the next layer which may be cement as in region 26 or water as in region 32). The duration over which significant reverberations last inside the casing walls 13-13' is a function of the casing thickness. Since casing of greater thickness tend to cause longer lasting reverberations, the total spacing D between the casing and receiver-transducer should be correspondingly increased.

When a window, which is normal to the direction of travel of the acoustic pulse, as suggested in dotted line at 42 in FIG. 1 is employed, the casing reflection and other acoustic returns produce reflections at the interface between window 42 and the mud inside casing 12. Such reflections appear as secondary transmissions which are returned to the casing to produce a second casing reflection with subsequent reverberations in the casing and thus also secondary acoustic returns. These secondary acoustic returns disturb the cement evaluation, particularly in case of a good cement bond when the formation also has a smooth surface. In this latter situation reflections caused by secondary reverberations mix with a significant reflection from the formation, giving an overall erroneous impression of a bad bond.

Hence, another criterion for determining an acceptable casing to receiver distance may involve selecting a distance $D_3$, between a window 42 and casing 12, such that secondary acoustic returns decay below a preselected percentage of their initial value. Thus, it can be shown that the number $N_r$, of reverberations in the steel casing 12 in such range is given by the relationship $$N_r = \frac{\ln(x)}{\ln(|r_0 r_1|)}$$

where x is the percentage fraction.

The distance $D_3$ can then be shown as given by the relationship $$D_3 > N_r L(C_0/C_l)$$

where L is the thickness of the casing 12, $C_0$ the velocity of sound of the material inside the casing, mainly water, and $C_1$ the velocity of sound in the casing, namely steel.

As a numerical example to arrive at an acceptable total casing to receiver distance, one may assume the values for the materials employed in the following Table 1.

TABLE 1

|  | Acoustic Impedance | Density | Velocity of Sound |
|---|---|---|---|
|  | Z in g/cm²sec | ρ in g/cm³ | C in ft/sec |
| water | $Z_0 = 1.5 \times 10^5$ | $\rho > 1$ | $C_0 = 4920$ |
| steel | $Z_1 = 4.6 \times 10^6$ | $\rho_1 = 7.8$ | $C_1 = 19,416$ |
| cement | $Z_2 = 7.7 \times 10^5$ | $\rho_2 = 1.96$ | $C_2 = 12,000$ |
| and $Z_2 = Z_0$ in case of a bad bond. | | | |

Using these constants the values for the reflection coefficients can be determined as $r_0 = 0.937$
$r_{1G} = -.731$ (for a good bond)
$r_{1B} = -.937$ (for a bad bond).

The casing to receiver distance or $D_3$ can be determined from the above constants and time setting constraints. For example, if the reverberations in the casing are to decay to about five percent of their initial value, the distance $D_3$ can be from about one and one-quarter inch to about three inches for a normally occurring range of casing thicknesses L from about 0.2" to about 0.65". By relaxing the final value of decay of the casing reverberations the source to casing distance can be decreased, though about one inch is likely to be a lowest possible limit for $D_3$. Since the largest casing thickness is preferably accommodated, the distance from the transducer 36 to either window 40 or 42 is chosen such that there is no secondary transmission interference over the time interval of interest. The distance $D_3$, when applicable, is chosen such that secondary reflections attributable to the window do not present signal interference. When the tool 20 employs a window such as 40, secondary reflections from such window are no longer a consideration in selecting the transducer to casing spacings.

In the selection of the transducer 36, a disk transducer having a diameter to wavelength ratio of greater than unity is employed. In practice, a disk transducer having a diameter of about one inch has been found useful. The transmitter pulse is formed of such duration and frequency as to stimulate a selected radial segment of the casing upon which the pulse is incident into a thickness resonance. Acoustic energy is transferred into the casing and reverberates in an enhanced manner with the duration and magnitude of reverberations highly sensitive to the layer of material adjacent the external surface of casing 12. Such sensitivity, however, should not include hydraulically secure micro-annuli such as at region 28.

In the selection of the frequency spectrum of the acoustic pulse from transducer 36, a primary basis is determined by the fundamental thickness resonance frequency of casing 12. Such resonance enables a trap mode with which enhanced acoustic energy is trapped in the casing. The subsequent reduction of trapped energy in the casing may be considered the result of leakage attributable to the degree of acoustic coupling to adjacent media. The frequency spectrum of the acoustic pulse should preferably include either the fundamental or a higher harmonic thereof. Expressed in mathematical terms, the stimulating frequency in the acoustic pulse is given by $$f_o = N(C_l/2L)$$

where $C_l$ is the casing compressional velocity and L is the casing thickness measured normal to the casing wall and N is a whole integer.

An upper limit of the frequency spectrum of the acoustic pulse is set by practical considerations such as casing roughness, grain size in the steel casing and mud attenuation. Furthermore, the hydraulically secure micro-annulus must appear transparent.

In practical cement bond applications a casing cement annulus equal or smaller than 0.005" (0.127 mm) represents a good cement bond and thus prevents hydraulic communications between zones intended to be separated. When annuli larger than this value occur, these should be construed as bad cement bonds. Furthermore, as long as an annulus is less in thickness than about 1/30 of a wavelength of an acoustic wave traveling in water, such annulus is effectively transparent to an acoustic wave of such wavelength. Hence, in terms of casing-cement annuli, the frequency spectrum of the acoustic pulse should be selected such that $$f_0 < \frac{C_0}{(\mu a_t) \times 30}$$

where $C_o$ is the velocity of sound in water and $\mu a_t$ is the thickness of the annulus.

In practical terms, casing thicknesses L normally encountered are from about 0.2" (5.08 mm) to about 0.65" (16.51 mm). Hence, with an effective frequency of from about 300 KHz to about 600 KHz for the acoustic pulse, the casing 12 can be stimulated into a trap mode which is insensitive to hydraulically secure microannuli. This frequency spectrum is selected so that the trap mode can be stimulated with either the fundamental frequency or its second harmonic for the thicker casings.

Within such frequency spectrum, the duration of the reverberations inside the steel casings become sensitive to both good and bad micro-annuli. For an acceptable micro-annulus the casing reverberations (and their observed leakage) decay more rapidly than for an excessively large micro-annulus.

The acoustic transmitter pulse is thus formed with characteristics as illustrated in FIGS. 2 and 3. The transmitter pulse 50 shown in FIG. 2 represents a highly damped acoustic pulse of a duration of the order of about eight microseconds. The frequency spectrum of such pulse 50 is shown in FIG. 3 with a frequency-amplitude curve 52 showing a 6 db (one-quarter power) bandwidth extending from about 275 KHz to about 625 KHz with a peak at about 425 KHz. The thick casings having a trap mode below 275 KHz are driven into resonance primarily with a higher harmonic such as the second which occurs with significant amplitude in the bandwidth of the spectrum 52.

The transmitter 36 can be formed of a variety of well known materials to produce pulse 50 with the frequency spectrum 52. For example, an electrical signal having these characteristics can be formed and amplified to drive a suitable piezoelectric transducer 36 capable of operating as a transmitter and receiver.

Preferably transducer 36 is formed with a piezoelectric disk crystal which is backed with a critically matched impedance such that an acoustic pulse is formed at the resonant frequency of the disk. The backing material has an impedance selected to match that of the crystal while strongly attenuating the acoustic pulse to avoid reflections from the back. In some applications a protective front layer may be employed integrally mounted on the front of the transducer 36. Such front layer is preferably made of a low attenuation material having an acoustic impedance which is approximately the geometric mean between the crystal impedance and the expected borehole fluid impedance. Such front layer has a quarter wavelength thickness as measured at the center resonant frequency of the crystal.

Since the disk is critically matched, the acoustic output pulse has a wide frequency bandwidth. Excitation of such transducer 36 may then be achieved with an electrical pulse of very short duration. For example, an impulse having a rise time of from about 10 to about 100 nanoseconds and a fall time of 0.5 to about 5 microseconds can be used.

In the transmitter mode transducer 36 may be actuated in a repetitive manner at a pulse rate, say, of the order of a hundred pulses per second. At such rate a circumferential region around casing 12 can be scanned as tool 20 is moved upward along the casing by making reflector 38 and its associated window 40 a rotatable mounting as illustrated for rotation in the direction of arrow 53.

Figure 5:
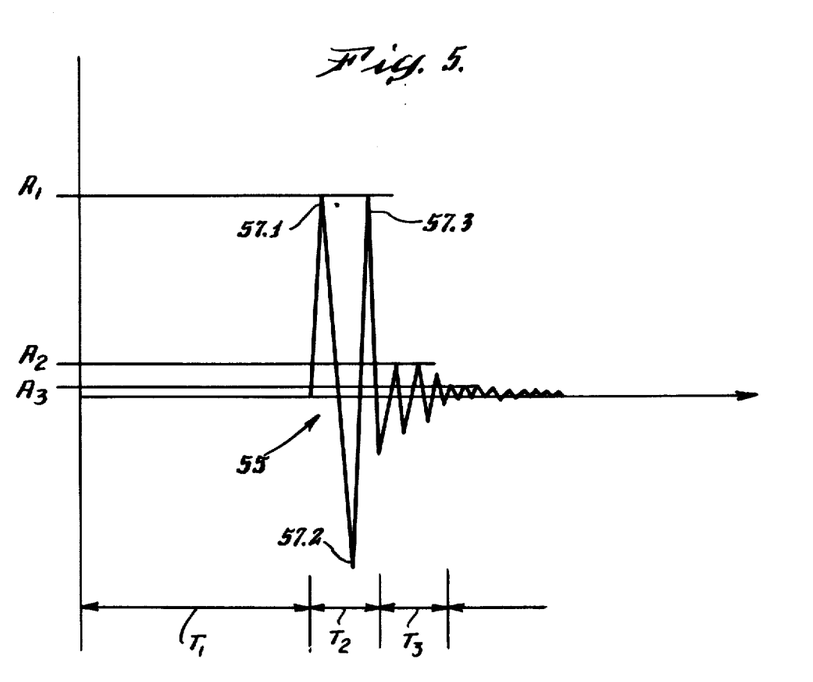
FIG. 5 is an amplitude response curve useful in specifying the performance requirement of a transducer preferred for use in an acoustic borehole investigation in accordance with the invention.

FIG. 5 defines the performance criteria for a suitable transducer 36. The transducer has a center acoustic frequency at about 425 KHz with a 6 db bandwidth of 300 KHz. The FIG. 5 illustrates an acceptable received amplitude response curve 55 when transducer 36 is energized with a pulse drive signal of about two microsecond duration and directed at a water/air interface spaced from the transducer at a distance equivalent to about 100 microseconds of two-way acoustic wave travel time, $T_1$. The output signal from transducer 36 as a result of the echo from the interface preferably should have an appearance as illustrated where the first echo, formed of the three main peaks 57.1, 57.2 and 57.3, should be of no greater total duration, $T_2$, than approximately six microseconds. The level $A_2$ of the noise immediately after the first echo should be about 50 db below the level $A_1$ of the peaks 57 and have a duration $T_3$ of less than about 30 microseconds. The noise level $A_3$ following interval $T_3$ preferably should be at least 60 db below the level $A_1$ of peaks 57.

The controls and circuitry necessary for firing of the transducer may originate from above ground equipment or from a suitable clock source located in tool 20. In either case, recurring synch pulses are produced on a line 54 of FIG. 1 to activate a pulse network 56 which generates a suitable pulse on line 58 to drive transducer 36 while simultaneously protecting the input 60 to amplifier 62 with a signal line 64.

The transducer 36 responds to the pulse from network 56 with an acoustic pulse of the type as shown in FIGS. 2 and 3. The acoustic pulse is directed onto reflector 38 which acts to direct the acoustic energy at the wall of casing 12. The effect of reflector 38 aids in compensating for variations in alignments of the acoustic pulse out of the plane normal to the casing wall. The reflector 38 can be a flat surface at an angle α of about 45° to the acoustic energy from transducer 36 or a slightly concave or convex surface.

When the acoustic pulse 50 impinges upon casing 12, some of the energy is reflected and some transferred into the casing 12. The reflected energy is returned to transducer 36 via reflector 38 and is reproduced as an electrical signal and applied to input 60 of amplifier 62.

The energy transferred into casing 12 reverberates, causing in turn further acoustic returns to transducer 36. The resulting received output from transducer 36 may have the appearance as illustrated with reflection signal waveforms 64, 66 and 68 in FIGS. 4A, 4B and 4C.

Figure 4A:
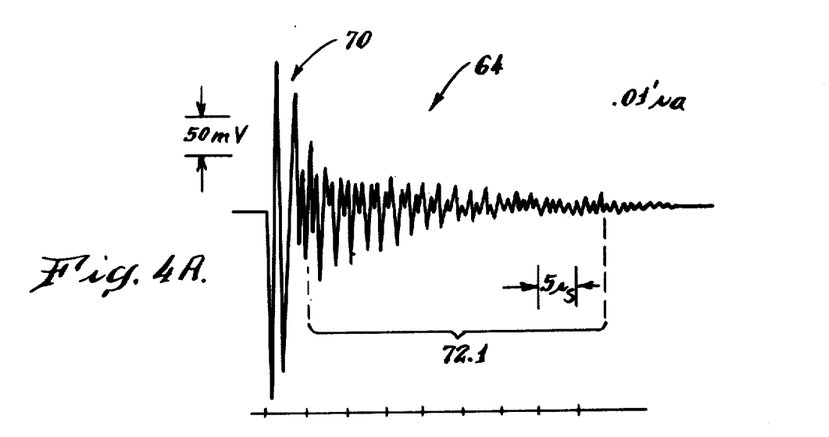
FIGS. 4A, 4B and 4C are illustrative waveforms representative of acoustic reflections obtained in a pulse-echo investigation technique conducted in accordance with the invention.
Figure 4B:
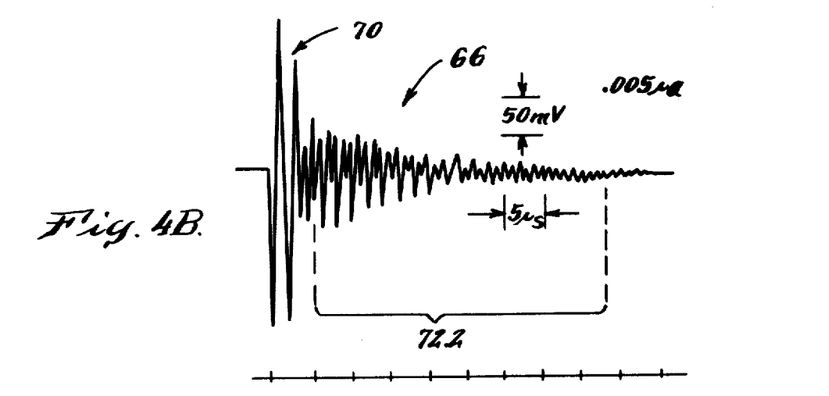
Figure 4C:
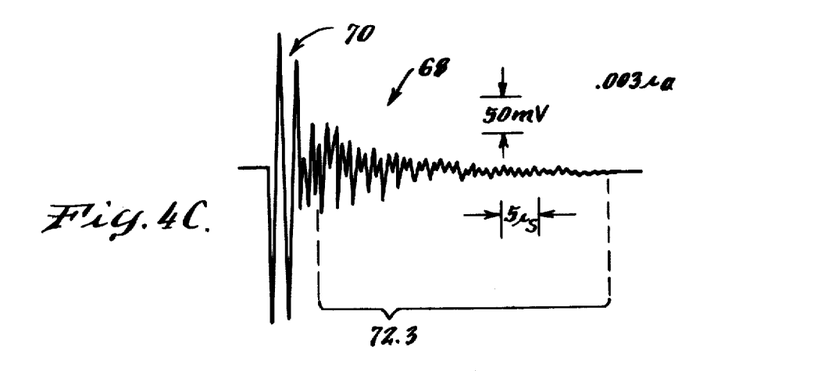

The initial segment 70 of each reflection signal waveform represents the strong initial casing reflection whose duration is of the order of about five microseconds. The remainder 72 is characterized as a reverberation segment in that it represents a large number of cycles of pulses representative of acoustic reverberations whose magnitudes decay over a period of time. The decay period varies as a function of the type of cement bond, as can be observed for waveforms 64, 66, 68 obtained with respectively differently sized annuli 30 around casing 12.

Except for the initial casing reflection segment 70, the reflection signals 64, 66, 68 do not have a highly predictive pattern wherein the peaks are precisely defined and extractable. Accordingly a prior art technique such as shown in the previously identified U.S. Patent to Norel et al. for comparing adjacent peaks to ascertain decay time constants for the waveforms is difficult to implement.

Instead, the signal processing segment 21 of the apparatus 10 operates on each reflection signal by separating the reverberation segment 72 from the initial strong acoustic casing reflection segment 70 and subsequently integrating the reverberation segment 72 over a particular time span to determine the energy therein.

In the embodiment of FIG. 1, the reflection signals from transducer 36 are amplified in amplifier 62 whose output is applied to a full wave rectifier 76 to produce on line 78 a DC signal representative of the amplitude of the received acoustic wave. The DC signals are filtered in a filter 80 to provide on line 82 a signal representative of the envelope of the waveforms from transducer 36.

The envelope signal on line 82 is applied to a threshold detector 84 which initiates subsequent signal processing by detecting the start of the initial casing reflection segment 70 (see FIG. 4). The amplitude at which the threshold detector 84 operates can be varied with a selector control applied to line 86 and can be automatically set.

The output on line 88 of threshold detector 84 is applied to activate an enabling pulse on output 90 from a pulse producing network 92. The pulse from this network 92 is selected of such duration that the envelope segment on line 82 and attributable to the initial casing reflection 70 is gated through an amplifier 94 as a casing reflection signal.

The duration of the enabling pulse on output 90 is selectable so that the entire casing reflection segment 70 can be selected in the event its duration varies. The DC form of the casing reflection signal is applied to an integrator network or peak amplitude detector 96 to produce a signal representative of the amplitude of the casing reflection 70 on line 98. This casing amplitude signal is stored such as with a sample and hold network 100 actuated by an appropriate pulse derived on line 102 from network 92 at the end of the pulse on line 90.

The output 88 from the threshold detector 84 is also applied to a reverberation segment selection network 103 including a delay 104 which produces an enabling pulse to pulse producing network 106 at a time after the initial casing reflection 70 has terminated. Network 106 generates a segment selection pulse on line 108 commencing at the beginning of the reverberation segment 72 and having a duration sufficient to gate the entire envelope form of the reverberation segment 72 (see FIG. 4) through gating amplifier 110 to integrator 112. The segment selection pulse on line 108 commences after the initial casing reflection and terminates after the desired number of acoustic returns of interest have been received but before secondary transmission interference arises. A typical pulse would start about six microseconds after the initial casing reflection is detected and would last for a period of about 40 microseconds after an acoustic pulse issued such as shown in FIGS. 2 and 3 and with a spacing D of the order of about three inches.

The integrator 112 integrates the envelope form for a time period determined by the pulse on line 108. At the end of this latter pulse a signal on line 114 from a pulse producer 106 activates a sample and hold network 116 to store a signal representative of the energy in the reverberation segment 72.

The outputs from sample and hold networks 100, 116 are applied to a combining network in the form of a divider 118 which forms a quotient by dividing the signal representative of the energy in the reverberation segment 72 by the normalizing signal indicative of the amplitude of the casing reflection 70 to generate a normalized energy bond signal on output line 120. The normalized energy signal on line 120 can be transmitted to above ground for recording reflection energy as a function of the depth on a plotter 122. The normalized energy signal may also be applied to a comparator 124 for comparison with a reference signal on line 126 derived from a network 128 and representative of the threshold level between good and bad cement bonds. The output 130 from comparator 124 indicates the presence or absence of a good cement bond can also be recorded on plotter 122 as a function of depth.

With the signal processing embodiments, the bond signal on line 120 is made less sensitive to tool tilts and attenuation in the fluid whereby the acoustic energy is directed at casing 12 along a plane which is skewed relative to the axis of the casing 12. When such condition occurs, the received acoustic returns are reduced in amplitude and may be interpreted as good cement bonds when, in fact, the cement bond may be bad. By employing the amplitude of the initial casing reflection as a gauge of tool tilt and mud conditions, the bond signal on line 120 provides a reliable indication of the cement bond quality.

There may in certain cases arise a need to obtain a bond signal which has not been normalized or which may be normalized at a later time. In such case the output 117 of the sample and hold network 116 is the bond signal which may be transmitted to above ground equipment for recording such as on a tape recorder or on plotter 122 or in the memory of a signal processor 130 after conversion to a digital form.

After a bond signal has been generated and a new synch pulse occurs on line 54, the synch pulse is applied to several reset inputs of sample and hold network 100, 116 and integrators 96, 112. The reset of the sample and hold networks 110, 116 can be delayed for a smoother output until such time as the outputs from integrators 96, 112 are ready for sampling.

The selection of a signal representative of the acoustic reverberation return 72 is obtained with a pulse produced on line 108 as can be determined with a segment selection network 132. This network controls the length of the delay 104 and the width of the enabling pulse from pulser 106. As previously described with reference to FIGS. 4A, 4B and 4C, the reverberation segment 72 is selected in such manner that the casing reflection 70 is effectively excluded.

This exclusion can be advantageously achieved by the signal processor 21 since it is activated by the detection of the strong casing reflection 70 as sensed by threshold detector 84. The resulting integration of the remaining envelope provides a sharp discrimination between a good bond signal and a bad bond signal. For example, the integration of the reverberation segment 72.1 of the waveforms 64 in FIG. 4A will be greater than the integration of the reverberation segment 72.3 of waveform 68 in FIG. 4C by a factor of about 3. When the area of the envelopes are compared for an example as set forth in Table 1, with the resulting reflection coefficients for $r_0$ and $r_1$ for good and bad cement bonds, an integration ratio of about 3.8-to-1 between bad and good signals occurs. Hence, an extremely sharp good-to-bad bond contrast is obtained which is likely to be obtained even in the presence of a dense mud inside the casing 12.

With certain types of cement one may wish to construe a micro-annulus of a thickness of the order of about 0.010 inches (0.25 mm) as a good cement bond. In such case, the frequency spectrum 52 of the acoustic pulse 50 may be adjusted to investigate the cement. One may, for example, employ two types of acoustic pulses of different frequency spectrum, one having the fundamental frequency and the other acoustic pulse having a harmonic. If the results from these pulses do not give the same reading, a hydraulically secure micro-annulus can be concluded to be present.

Theoretically a bond will appear as good for a microannulus having a thickness of the order of half wavelength (about 0.08 inches). However, in practice such large annulus is unlikely to arise and other conventional cement quality investigation techniques can be employed to identify such unlikely large annulus as a poor cement bond.

Figure 6:
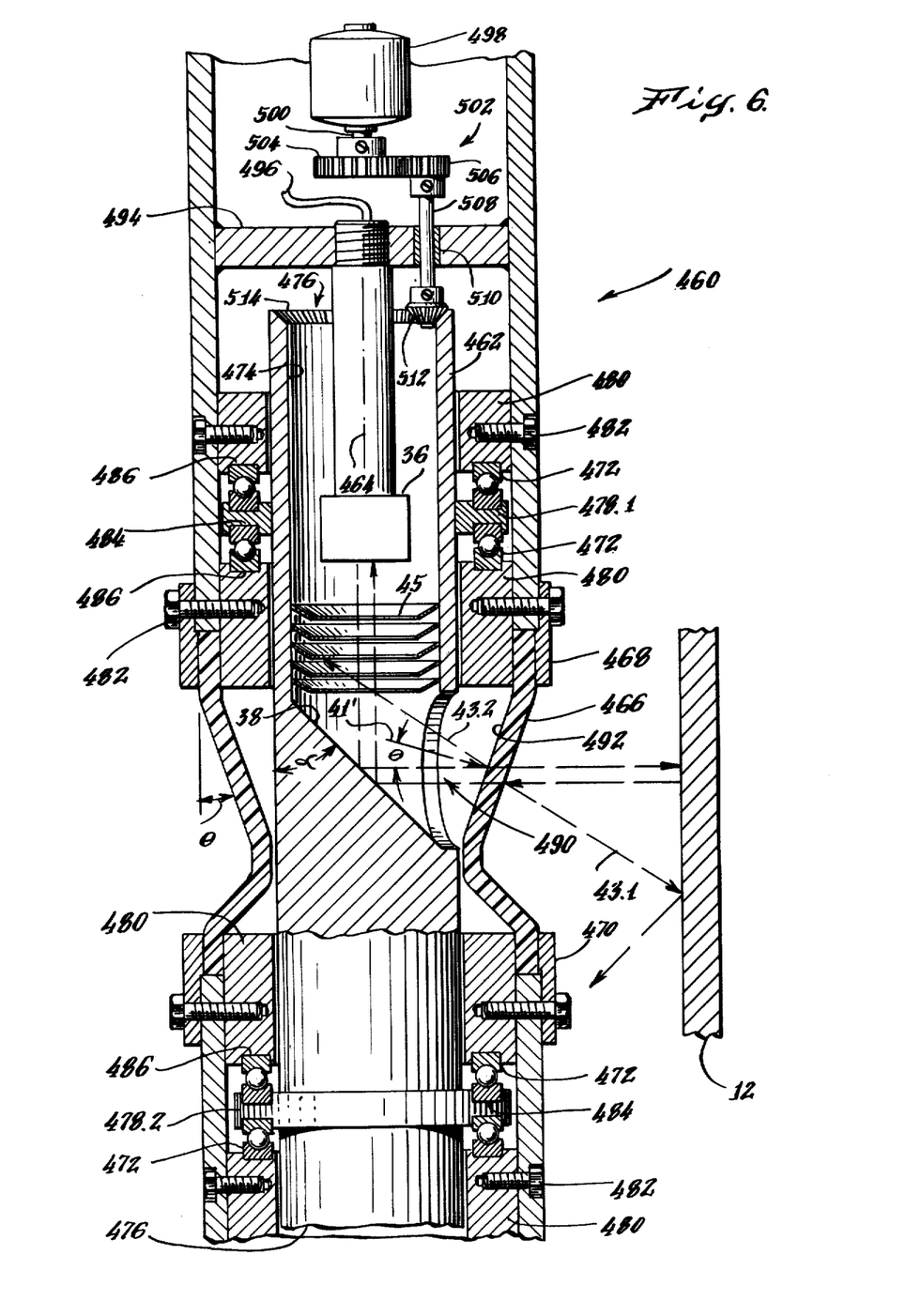
FIG. 6 is a sectional view of an acoustic borehole investigating tool employing a rotating reflector for scanning of the borehole.

FIG. 6 illustrates another form 460 for an acoustic cement bond and casing investigating tool, wherein as in FIG. 1, a rotating reflector 38 is employed. The tool 460 is provided with a stationary transducer 36 and a longitudinal cylinder 462 centrally and rotatably mounted relative to tool 460 about a rotational axis 464 which in this embodiment is preferably coincident with the central tool axis.

The tool 460 has an annular acoustically transparent window 466 mounted between an upper tool section 468 and a lower tool section 470. The cylinder 462 internally bridges the window 466 and rotationally engages the upper and lower sections 468, 470 through bearings 472.

The cylinder 462 has a tubular section 474 into which transducer 36 projects through an open end at 476. The tubular section 474 terminates at reflector 38 from where the cylinder 462 preferably is solid down to its end 476. Cylinder 462 is provided with a pair of annular radially extending flanges 478.1 and 478.2. Bearings 472 are clamped against flanges 478 with annular bushings 480 affixed to tool sections 468, 470 with screws such as 482. Bearings 472 fit in axially open annular grooves 484, 486 in flanges 478 and bushings 480 respectively. Bearings 464 provide both thrust and radial low friction support. Additional bearings and flanges can be employed if needed.

Cylinder 462 is of rugged strong construction to reinforce the lower tool section 470 to which a load producing device, such as an externally mounted centralizer (not shown), can be applied. The cylinder 462, thus serves as a strong reinforced bridge over acoustic window 466. The ability to employ a centralizer below the rotating reflector 38 enables a precise placement of the rotational axis 464 relative to the casing 12 and thus preserve an accurate spacing of reflector 38 from casing 12.

The acoustic reflector 38 has a reflection angle α of a magnitude necessary to enable acoustic communication through a side-located opening 490 in tubular section 474. In front of opening 490 and contiguous with the outer wall of upper tool section 468 is the acoustic window 466 formed of a material having a predetermined acoustic impedance and provided with a shape selected to minimize undesirable acoustic reflection.

The acoustic window 466 is formed of a material whose acoustic impedance closely matches the acoustic impedance of a fluid, such as described with reference to FIG. 1, and which is placed in the space between source 36, reflector 38 and window 466. The acoustic temperature and pressure coefficients, i.e. the change in acoustic impedance as a function of temperature and pressure for both the fluid and the window 466 are selected as close as practically possible. The acoustic window 466 can be made of a material as described with reference to window 40 in FIG. 1 or of polysulfone, a material sold by the Union Carbide Corporation under the trade name RADEL and having an acoustic velocity of about 2200 meters/second. Hence, as an acoustic pulse is generated from source 36 towards reflector 38, the acoustic energy passes through the fluid/window interface 492 with a minimum of reflection.

In order to further reduce the effect of acoustic reflections from a window interposed between the source 36 and casing 12, the window is conically shaped with an inclination angle θ relative to reflector 38 as described with reference to FIG. 1 to permit use of a large reflector 38 and also to deflect secondary transmissions away from the casing 12.

Transducer 36 in FIG. 6 is mounted to a bracket 494 attached to the wall of tool section 468. An electrical cable 496 connects transducer 36 to electronic circuitry (not shown).

A rotational drive for cylinder 462 is provided by an electrical motor 498 mounted inside tool 460 and having an output shaft 500. A gear coupling 502 interconnects the motor shaft 500 to the cylinder 462.

The gear coupling 502 may take a variety of different forms and is, for illustrative purposes, shown composed of a pair of pinions 504, 506, with the latter mounted to a shaft 508 journaled in a bushing 510 on bracket 494. A bevel drive, formed of 45° bevel gears, 512, 514, is used to interconnect the shaft 508 with cylinder 462.

With a tool 460 as shown in FIG. 6, the structural integrity of the tool is extended to below the annular window 466. This provides additional strength below the window and permits its centralization relative to casing 12 with a centralizer. Window 466 can be made sufficiently strong to withstand such twisting forces as may be coupled through from the rotating cylinder 462.

Having thus explained techniques for investigating a casing cemented in a borehole to evaluate the cement bond and casing thickness, the advantages of the invention can be appreciated. Variations from the described embodiments presented herein are for illustration, with the scope of the invention to be determined by the following claims.

What is claimed is:

1. In an acoustic borehole investigating tool having an acoustic transducer for directing acoustic energy at a rotating reflector to acoustically investigate a radially remote wall with acoustic returns being reflected off the rotating reflector onto the acoustic transducer, the improvement comprising said tool being formed of upper and lower tool sections;

an annular acoustically transparent window mounted to and between the upper and lower tool sections;

a cylinder mounted for rotation about an axis to and inside the upper tool section and having sufficient axial length to internally bridge the annular transparent window and rotatably engage and structurally reinforce the lower tool section at the inside thereof, said cylinder having a tubular section with a side located opening radially opposite said annular transparent window, said tubular section commencing at the upper tool section and internally supporting said reflector radially opposite said side located opening to enable acoustic communication through the annular window.

2. The improved acoustic borehole investigating tool as claimed in claim 1 wherein the cylinder is in the form of a solid rod below the reflector for enhanced reinforcement of the lower tool section.

3. The improved acoustic borehole investigating tool as claimed in claim 2 wherein the annular window has a conical shape with a conical angle which has a positive angle of inclination relative to the travel path of acoustic energy from the reflector.

4. The improved acoustic borehole investigating tool as claimed in claim 3 wherein the acoustic transducer extends into the tubular section of the cylinder facing the reflector, and a plurality of annular acoustic baffles are spaced between the transducer and the reflector.

* * * * *